US012622706B2

(12) United States Patent
Harris et al.

(10) Patent No.: US 12,622,706 B2
(45) Date of Patent: May 12, 2026

(54) EXTENDIBLE AND RETRACTABLE ENDOSCOPIC CAP

(71) Applicant: BOSTON SCIENTIFIC SCIMED, INC., Maple Grove, MN (US)

(72) Inventors: Colby Harris, Norfolk, MA (US); Allison Kumarasena, Wellesley, MA (US); Jennifer Lewitzky, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 154 days.

(21) Appl. No.: 18/753,572

(22) Filed: Jun. 25, 2024

(65) Prior Publication Data

US 2025/0057541 A1      Feb. 20, 2025

Related U.S. Application Data

(60) Provisional application No. 63/520,498, filed on Aug. 18, 2023.

(51) Int. Cl.
| | |
|---|---|
| *A61B 17/128* | (2006.01) |
| *A61B 1/00* | (2006.01) |
| A61B 17/00 | (2006.01) |
| A61B 17/12 | (2006.01) |

(52) U.S. Cl.
CPC ...... *A61B 17/1285* (2013.01); *A61B 1/00137* (2013.01); *A61B 2017/00115* (2013.01); *A61B 2017/00367* (2013.01); *A61B 2017/12004* (2013.01)

(58) Field of Classification Search
CPC . A61B 17/10; A61B 17/1227; A61B 17/1285; A61B 1/00089; A61B 1/00133; A61B 1/00135; A61B 1/00137; A61B 1/0014; A61B 2017/00115; A61B 2017/00367; A61B 2017/12004
See application file for complete search history.

(56) References Cited

U.S. PATENT DOCUMENTS

| | | | | |
|---|---|---|---|---|
| 5,002,042 A | * | 3/1991 | Okada | A61B 1/042 |
| | | | | 600/127 |
| 6,042,591 A | * | 3/2000 | Mears | A61B 17/12013 |
| | | | | 606/140 |
| 8,152,822 B2 | * | 4/2012 | Gayzik | A61B 17/1227 |
| | | | | 606/151 |
| 8,882,659 B2 | | 11/2014 | Naito | |

(Continued)

*Primary Examiner* — Ryan J. Severson
(74) *Attorney, Agent, or Firm* — Fay Kaplun & Marcin, LLP

(57) ABSTRACT

A tissue treating device includes a handle with an actuator; a control cable; and a cap. The cap includes a mounting structure removably coupled in an operative configuration on a distal end of an insertion device. The cap includes a part movably coupled to the structure for movement between a retracted position in which a distal end of the part is received over the distal end of the device and an extended position in which a distal end of the part extends distally beyond the distal end of the device. The part includes a wall defining an internal channel so that, when the part is in the extended position, the wall surrounds a space contiguous to the distal end of the device. The part is coupled to a distal end of the cable so that, actuation of the actuator moves the part between the extended and retracted positions.

18 Claims, 5 Drawing Sheets

(56)  References Cited

U.S. PATENT DOCUMENTS

| | | | | |
|---|---|---|---|---|
| 8,945,153 | B2 * | 2/2015 | Surti | A61B 50/13 |
| | | | | 606/142 |
| 9,949,619 | B2 * | 4/2018 | Iizuka | A61B 1/00098 |
| 10,743,745 | B2 | 8/2020 | Chae | |
| 11,849,930 | B2 * | 12/2023 | Congdon | A61B 17/1285 |
| 12,127,742 | B2 * | 10/2024 | Favreau | A61B 1/00089 |
| 12,232,697 | B2 * | 2/2025 | Adhikarath Balan | |
| | | | | A61B 1/00137 |
| 2007/0282353 | A1 * | 12/2007 | Surti | A61B 17/1285 |
| | | | | 606/142 |
| 2010/0016873 | A1 * | 1/2010 | Gayzik | A61B 17/1227 |
| | | | | 606/151 |
| 2013/0231531 | A1 * | 9/2013 | Naito | A61B 1/00089 |
| | | | | 600/129 |
| 2016/0174814 | A1 * | 6/2016 | Igov | A61B 1/00101 |
| | | | | 600/106 |
| 2016/0338681 | A1 * | 11/2016 | Smith | A61B 1/273 |
| 2016/0374537 | A1 * | 12/2016 | Chae | A61B 1/00089 |
| | | | | 600/127 |
| 2017/0164815 | A1 | 6/2017 | Smith et al. | |
| 2021/0022740 | A1 | 1/2021 | Favreau et al. | |
| 2022/0110618 | A1 | 4/2022 | Congdon et al. | |
| 2023/0027249 | A1 | 1/2023 | Adhikarath Balan et al. | |
| 2024/0130721 | A1 * | 4/2024 | Gole | A61B 17/00491 |
| 2024/0225628 | A9 * | 7/2024 | Gole | A61B 17/00491 |
| 2024/0307044 | A1 * | 9/2024 | Gole | A61B 1/00101 |
| 2025/0057541 | A1 * | 2/2025 | Harris | A61B 17/1227 |
| 2025/0143549 | A1 * | 5/2025 | Kumarasena | A61B 1/00137 |

* cited by examiner

EXTENDIBLE AND RETRACTABLE ENDOSCOPIC CAP

PRIORITY CLAIM

The present disclosure claims priority to U.S. Provisional Patent Application Ser. No. 63/520,498 filed Aug. 18, 2023; the disclosure of which is incorporated herewith by reference.

FILED

The present disclosure relates to endoscopic devices and, in particular, relates to a cap for attachment to a distal end of an endoscope.

BACKGROUND

Physicians have become more willing to perform a wide variety of interventional and therapeutic endoscopic gastrointestinal (GI) procedures in which tissue adjacent to a distal end of an endoscope must be observed and/or treated. Certain of these procedures involve a cap that is coupled to the distal end of the endoscope to extend distally away from the distal end of the endoscope to provide a space, for example, into which tissue may be drawn for treatment or which may be used to observe tissue free from certain conditions outside the cap, etc.

SUMMARY

The present disclosure relates to a device for treating tissue. The device includes a handle including a first actuator; a first control cable extending distally from a proximal end coupled to the first actuator; and a cap. The cap includes a mounting structure configured to be removably coupled in an operative configuration on a distal end of an insertion device. The insertion device is configured to be inserted to a target site within a living body.

The cap further includes an extending part movably coupled to the mounting structure for movement between a retracted position in which a distal end of the extending part is received over the distal end of the insertion device and an extended position in which a distal end of the extending part extends distally beyond the distal end of the insertion device. The extending part includes a wall defining an internal channel so that, when the extending part is in the extended position, the wall surrounds a space contiguous to the distal end of the insertion device, the extending part being coupled to a distal end of the first control cable so that, actuation of the first actuator moves the extending part between the extended and retracted position.

In an embodiment, the extending part is slidably received over the mounting structure so that the extending part moves linearly along the mounting structure between the extended and retracted positions.

In an embodiment, the first control cable is configured to be mounted along a length of the insertion device to extend from the cap to the handle and wherein the handle is configured to remain, during use, outside the living body accessible to a user.

In an embodiment, the mounting structure includes a thread and the extending part includes a structure mating with the thread so that rotation of the extending part about the mounting structure in a first direction moves the extending part distally relative to the mounting structure and rotation of the extending part about the mounting structure in a second direction opposite the first direction moves the extending part proximally relative to the mounting structure.

In an embodiment, the first control cable is configured to be inserted through an internal channel of the insertion device to the distal end thereof, the first control cable passing into the extending part via an opening in a radially inner surface of the wall of the extending part and being mounted to the extending part so that, movement of the first actuator moves the first control cable relative to the mounting structure to rotate the extending part about the mounting structure to move the extending part proximally and distally relative to the distal end of the insertion device, the handle being configured to remain, during use, outside the living body accessible to a user.

In an embodiment, the handle further includes at least one feedback structure configured to interact with the first actuator so that a user receives feedback corresponding to actuation of the first actuator corresponding to an amount of movement of the extending part relative to the mounting structure.

In an embodiment, the first actuator is slidably mounted on a body of the handle and the feedback structure includes a series of bumps on the body of the handle which, when contacted by the first actuator, provide tactile or audible feedback to the user.

In an embodiment, the first actuator comprises a wheel coupled to the first control cable and rotatably mounted on the handle so that rotation of the wheel rotates the first control cable.

In an embodiment, the device further includes a hemostatic clip removably mounted on the extending part and a second control cable extending from the hemostatic clip to a second actuator on the handle so that, when the extending part is moved to the extended position, operating the second actuator moves the second control cable to deploy the hemostatic clip from the extending part to clip any tissue drawn into the channel of the extending part.

In an embodiment, the first control cable includes a longitudinally stiff axially flexible coil.

In an embodiment, the mounting structure includes a first portion having a first outer diameter and a second portion extending distally from the first portion and having a second outer diameter reduced relative to the first outer diameter of the first portion and the extending part having an inner diameter corresponding to the second outer diameter of the second portion and an outer diameter substantially equal to that of the first portion.

In an embodiment, the hemostatic clip includes first and second jaws biased toward a closed configuration and wherein the extending part is sufficiently radially stiff to maintain the hemostatic clip in an open configuration in which the first and second jaws are separated from one another and so that the channel of the extending part remains open to receive tissue to be clipped when in the extended position.

In addition, the present disclosure relates a method for treating tissue. The method includes mounting on a distal end of an endoscope a mounting structure of a cap in a retracted position in which a distal end of the cap is retracted toward the distal end of the endoscope; advancing the endoscope into a living body to a target site adjacent to tissue to be treated; operating a first actuator which, during use, remains outside the living body accessible to a user, to extend an extending part of the cap distally relative to the mounting structure so that the extending part projects distally from the distal end of the endoscope with an internal channel of the extending part defining an interior space contiguous with the distal end of the endoscope; and after treating tissue accessed via the internal channel of the extending part, operating the first actuator to retract the extending part to the retracted position.

In an embodiment, operating the first actuator to extend the extending part of the cap distally relative to the mounting structure comprises sliding the first actuator axially relative to a body of a handle on which the first actuator is mounted.

In an embodiment, operating the first actuator to extend the extending part of the cap distally relative to the mounting structure comprises rotating the first actuator about a body of a handle on which the first actuator is mounted.

In an embodiment, the cap includes a hemostatic clip removably received thereon. The method further includes drawing tissue into the internal channel of the extending part; and operating a second actuator that, during use, remains outside the living body accessible to the user, to deploy the hemostatic clip from the extending part to clip the tissue that has been drawn into the internal channel of the extending part.

In an embodiment, actuation of the first actuator moves the extending part linearly over the mounting structure.

In an embodiment, the method further includes actuating the first actuator in a first direction to rotate the extending part over a threading of the mounting structure to advance the extending part distally relative to the mounting structure; and actuating the first actuator in a second direction opposite the first direction to rotate the extending part linearly over the threading of the mounting structure to retract the extending part proximally relative to the mounting structure.

BRIEF DESCRIPTION

DETAILED DESCRIPTION

Figure 1A:
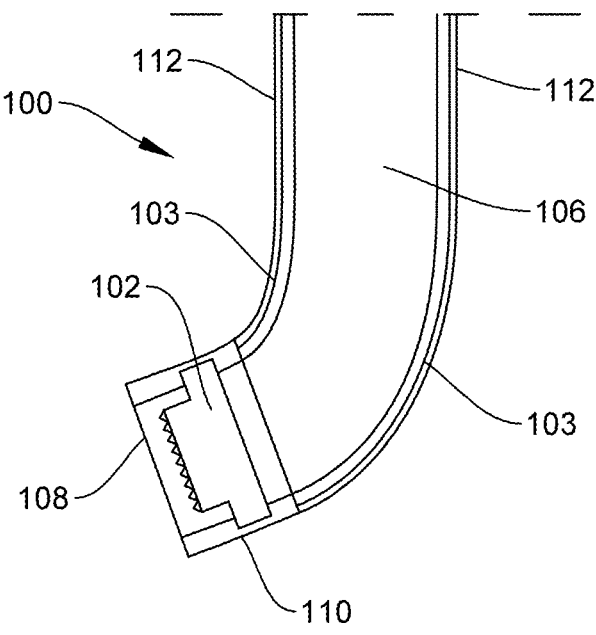
FIG. 1A shows side view of an endoscope having mounted thereon a cap according to an illustrative embodiment in a retracted state.
Figure 1B:
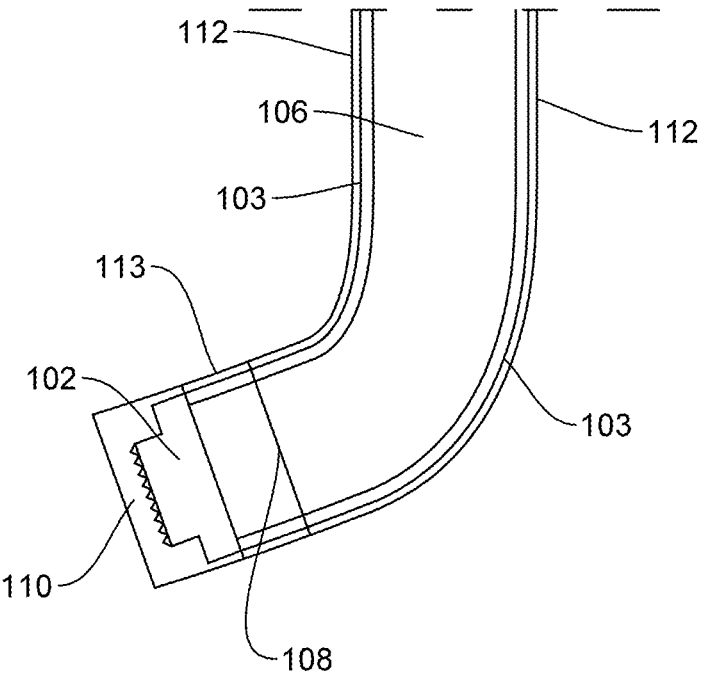
FIG. 1B shows a side view of an endoscope having mounted thereon the cap of FIG. 1A in an extended state.
Figures 2A, 2B:
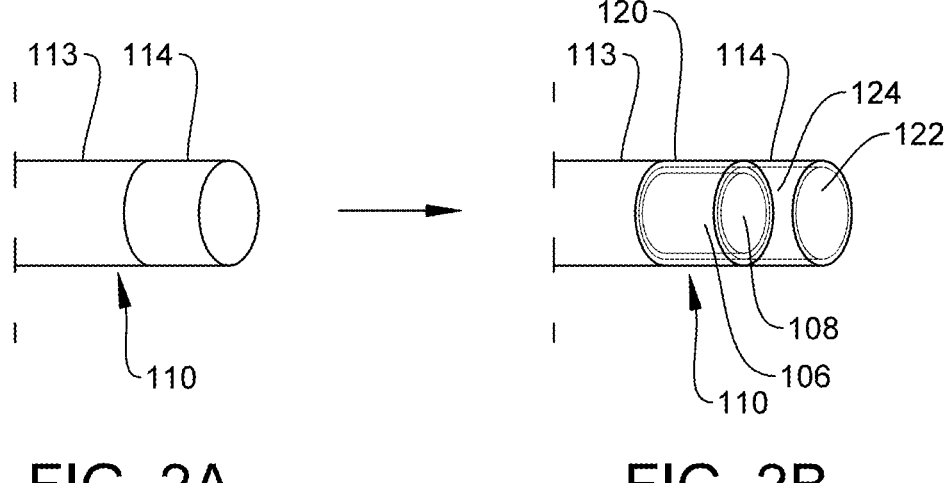
FIG. 2A shows a perspective view of the cap of FIGS. 1A and 1B in the retracted state.
FIG. 2B shows a perspective, partially transparent view of the cap of FIGS. 1A and 1B in the extended state.
Figure 3:
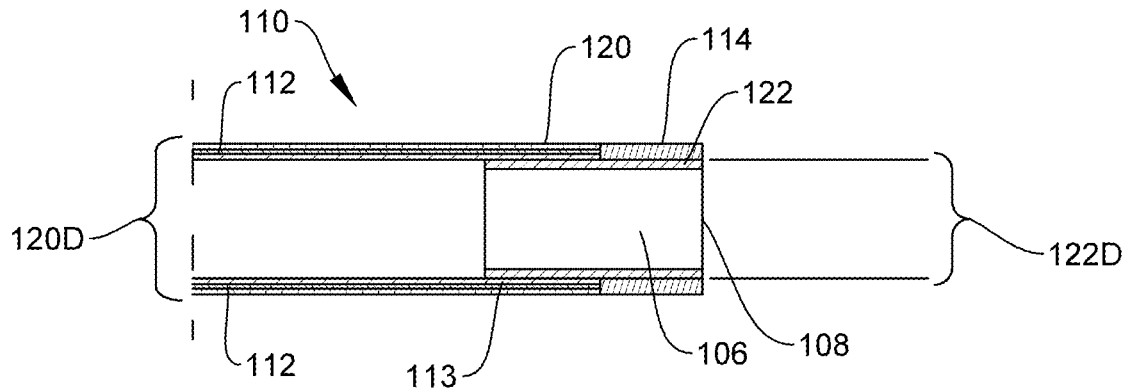
FIG. 3 shows a cross-sectional view of the cap of FIGS. 1A and 1B in the retracted state.
Figure 4:
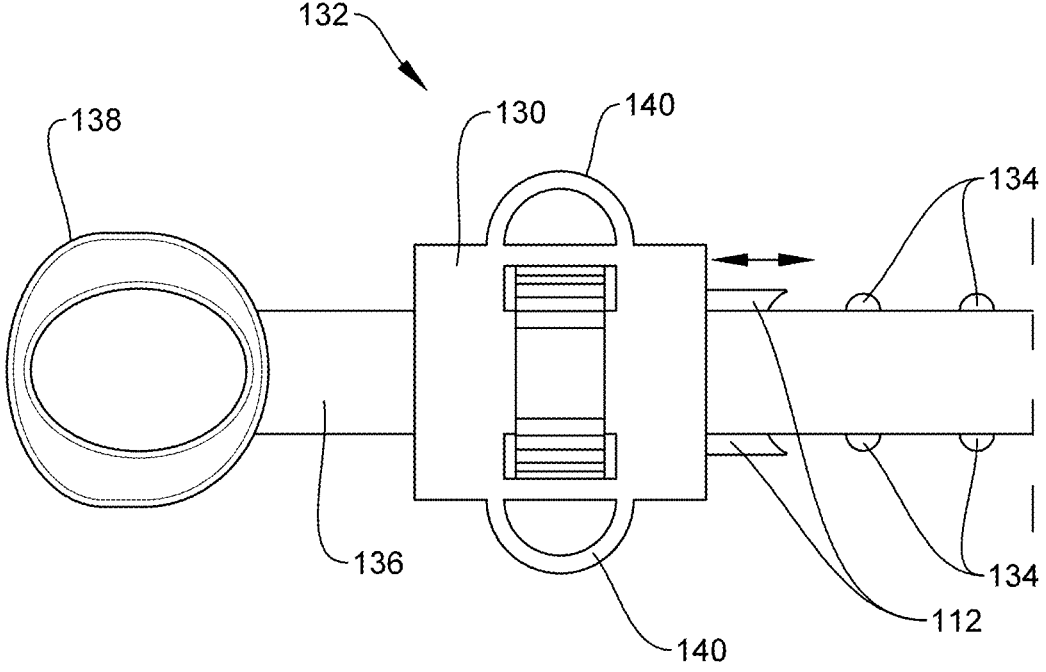
FIG. 4 shows a side view of handle and actuator for use with the system of FIGS. 1-3.

The present disclosure may be further understood with reference to the following description and the appended drawings, wherein like elements are referred to with the same reference numerals. The present disclosure relates to a cap that is selectively coupleable to the distal end of an endoscope or other insertion device to create a controllable space distal to a distal end of the endoscope wherein the controllable space may be employed, e.g., to create an area of enhanced visibility distal to the endoscope, to provide a space into which tissue may be drawn so that the tissue may be treated in any of a variety of procedures, to create space between the distal end of the scope and tissue to be observed, treated, sampled or otherwise interacted with.

Exemplary embodiments will describe this cap in use in conjunction with an over the scope hemostatic clip. However, those skilled in the art will understand that the cap according to these embodiments may be employed for any number of uses related to or unrelated to hemostatic clips. Furthermore, as will be understood by those skilled in the art, the terms distal and proximal are employed in this application to indicate directions—proximal (toward a user) and distal (away from a user).

As would be understood by those skilled in the art, the adapters according to the described embodiments may be used in a wide range of applications including the deployment of ligating bands, procedures in which a user may wish at one point to observe tissue up close (i.e., with an adapter withdrawn proximally onto the endoscope) and at another point, to create a controlled space distal of the distal end of the endoscope. For example, in certain situations, a physician may wish to create space between the vision system of the endoscope and tissue to be examined, or the physician may wish to clear the area in front of the endoscope to enhance vision (e.g., by aspirating debris from the space within the adapter). In some cases, the physician may be inserting the endoscope into a space between layers of tissue which would collapse on the endoscope leaving no space for visualization. Extending the adapter distally from the endoscope may create the separation from the tissue necessary to enable observation.

Such a procedure may involve, for example, the injection of fluid into an organ wall between layers of the tissue of the organ to separate the layers. The physician may then make an incision in the organ wall and insert the endoscope into the space between the layers of tissue (e.g., to see if a lesion has penetrated into deeper layers of the tissue). This observation may be enhanced through the extension of an adapter as described below from the distal end of the endoscope to create a desired amount of space between the lens of the endoscope and the tissue. Thus, there are many procedures which may be enhanced through the use of the adapters described below and the discussion of hemostatic clips is exemplary only.

As shown in FIGS. 1-4, a clipping system 100 for treating tissue defects and/or perforations according to an exemplary embodiment includes an adapter 110 mounted over the distal end 108 of an endoscope 106. The adapter 110 includes a proximal mounting portion 113 configured to be removably mounted on the distal portion of the endoscope 106 (e.g., via a friction fit) and a telescoping distal portion 114 movably mounted to the proximal mounting portion 113.

As would be understood by those skilled in the art, a cap coupled to an endoscope so that it extends distally from the distal end of the endoscope may reduce a field of view of the endoscope and may make it more difficult to maneuver the endoscope through a body lumen to a target site (e.g., by making it more difficult to navigate tight bends). The adapters of the embodiments described herein are movable relative to the endoscope to move between a retracted configuration and an extended configuration. This permits a user to retract the adapter to the retracted state when the user wishes to view a wider or unobstructed field of view or to enhance the maneuverability of the endoscope by eliminating all or part of the distal projection of the adapter beyond the distal end of the endoscope.

For example, in this embodiment, the adapter 110 is movable relative to the distal end 108 (e.g., slidable axially along the endoscope 106) of an endoscope 106 on which the adapter 110 is mounted via extending members 112 each of which extends from a distal end coupled to the adapter 110 along the outside of the endoscope 106 to a proximal end coupled to an actuator 130 on a handle 132. As will be described below, when the adapter 110 is configured to deploy, for example, an over the scope hemostatic clip 102, one or more of the extending members 112 may be config- ured as a hollow member (e.g., a longitudinally stiff, axially flexible coil) within which a control wire is slidably received to actuate the clip 102 in any known manner. That is, as would be understood by those skilled in the art, each of the control wires 103 may extend distally beyond a distal end of the corresponding extending member 112 to releasably couple to the clip 102 so that the clip may be deployed over target tissue that has been drawn into the adapter 110 in any known manner.

The proximal ends of the extending members 112 are coupled to the actuator 130 that is slidably mounted on the body 136 of the handle 132. The body 136 of the handle 132 includes a series of feedback bumps 134 which provide tactile and/or audible feedback to the user as the actuator 130 is advanced distally so that the user knows with each bump 134 encountered how far the adapter 110 has been advanced distally from an initial position (e.g., a fully retracted position in which a distal end of the adapter 110 is aligned with the distal end of the endoscope 106). The handle 132 of this embodiment includes a finger loop 138 while the actuator 130 includes a pair of finger loops 140.

However, those skilled in the art will understand that the handle 132 may take any configuration that allows an operator to move the actuator 130 relative to the body 136 of the handle 132 as desired to achieve the desired move- ment of the adapter 110. Those skilled in the art will understand that the actuator 130 may also include a locking mechanism so that the position of the actuator 130 relative to the body 136 of the handle 132 may be locked which will the lock the position of the adapter 110 relative to the distal end 108 of the endoscope 106.

As would be understood by those skilled in the art, the system 100 may be used in conjunction with any over the clip 102 and so the operation of the clip 102 will not be described in detail except as it relates to the movement of the adapter 110 between the retracted and extended configura- tions. That is, those skilled in the art will understand that, once the adapter 110 is in the extended configuration, the operation of the clip 102 will be substantially the same as it would have been at all times on a prior system including an adapter that remains fixed in a position extending distally from the endoscope.

In this embodiment, the telescoping distal portion 114 of the adapter 110 is slidably received on the proximal mount- ing portion 113 for movement proximally and distally there- over between the retracted and extended configurations (or to any desired partially extended configuration). Specifi- cally, in this embodiment, the proximal mounting portion 113 includes a first portion 120 having a first outer diameter 120D and a second portion 122 extending distally from the first portion 120 and having an outer diameter 122D reduced relative to the outer diameter of the first portion 120. The telescoping distal portion 114 of this embodiment has an inner diameter corresponding to the outer diameter of the second portion 122 and an outer diameter substantially equal to that of the first portion 120. As would be understood by those skilled in the art, though this is not necessary it ensures that the cross-sectional area of the adapter 110 is minimized to reduce interference with surrounding tissue as the endo- scope 106 is inserted to the target site.

The proximal mounting portion 113 of the adapter 110 of this embodiment is a hollow member sized and shaped to be friction fit over the distal end of the endoscope 106 and is radially stiff enough so that when the clip 102 is received on the telescoping distal portion 114, jaws of the clip are spread apart from one another keeping a central channel 124 of the telescoping distal portion 114 open, even when the telescop- ing distal portion 114 is extended distally from the retracted configuration, to receive target tissue and to minimize any reduction in the field of view of the endoscope by the telescoping distal portion 114.

In use, the adapter 110 is mounted on the endoscope 106 by sliding the first portion 120 over the distal end 108 of the endoscope 106 until the distal end of the telescoping distal portion 114 is flush with the distal end 108 of the endoscope 106. The extending members 112 are then drawn proximally along the endoscope 106 and, optionally, secured thereto. The adapter 110 is maintained in the retracted configuration as the endoscope 106 is then navigated to a target site within the body (e.g., through a body lumen accessed via a natu- rally occurring bodily orifice). Those skilled in the art will understand that this allows the user to maintain all of the advantages of maneuverability and field of view of the endoscope 106 during the insertion of the endoscope 106 to the target site.

When the target site is reached, the user may maintain the adapter in the retracted configuration to observe the target tissue and, when the user has identified a desired location at which the clip 102 is to be deployed, the user may move the extending members 112 distally so that the extending mem- bers 112 push the telescoping distal portion 114 distally over the second portion 122 of the proximal mounting portion 113 so that the telescoping distal portion 114 slides over the second portion 122 to the extended configuration. Those skilled in the art will understand that a maximum distal extension of the telescoping distal portion 114 may be defined by a limit on the movement of the extending members 112 or, e.g., by a shoulder of the second portion 122 positioned to abut a corresponding shoulder of the telescoping distal portion 114 or by any other known mecha- nism.

When the telescoping distal portion 114 is in the desired position (e.g., extended fully to the extended configuration or extended to any desired intermediate position), the user may draw target tissue into the central channel 124 (e.g., via suction applied through a working channel of the endoscope 106) and deploy the clip 102 from the adapter 110 to clip this tissue. The user may then retract the telescoping distal portion 114 to the retracted configuration by operating the actuator 130 on the handle 132 to retract the extending members 112 proximally and remove the endoscope 106 from the body.

Figure 5:
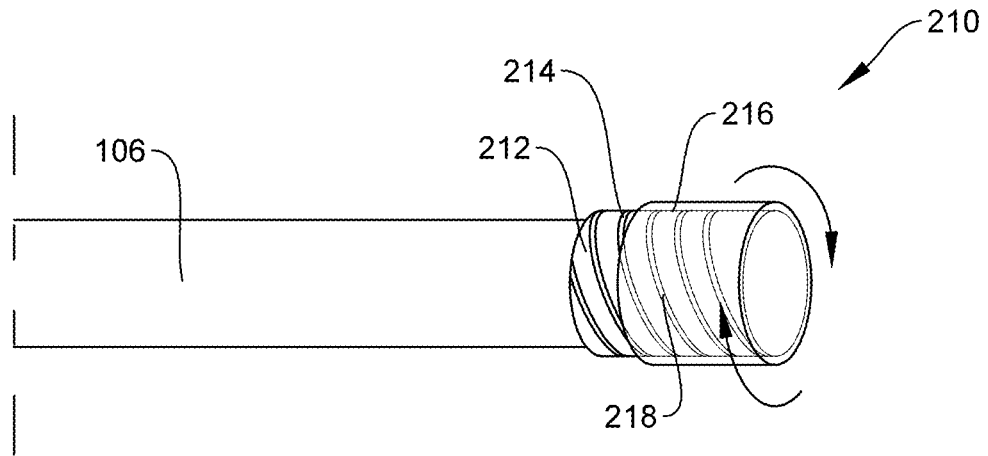
FIG. 5 shows a perspective view of a cap according to a further embodiment.

As shown in FIG. 5, an adapter 210 according to a further embodiment including an inner member 212 with a helical ridge 214 protruding therefrom. An outer cap 216 mounted over the inner member 212 includes a helical groove 218 that slidably receives the ridge 214 so that the cap 216 may be advanced distally and retracted proximally over the inner member 212 by rotation of the cap 216 over the ridge 214. Those skilled in the art will understand that this screw mechanism allows a user to achieve any known amount of extension of the cap 216 as the distance the cap is extended distally or retracted proximally per rotation of the cap 216 is known based on the pitch of the ridge 214 and the helical groove 218. Thus, a user may simply rotate the cap 216 by the number of degrees corresponding to the desired amount of distal extension or proximal retraction of the cap 216. For example, if a user may rotate the cap manually before inserting the instrument into the body to a desired extension of the cap 216.

Figure 6:
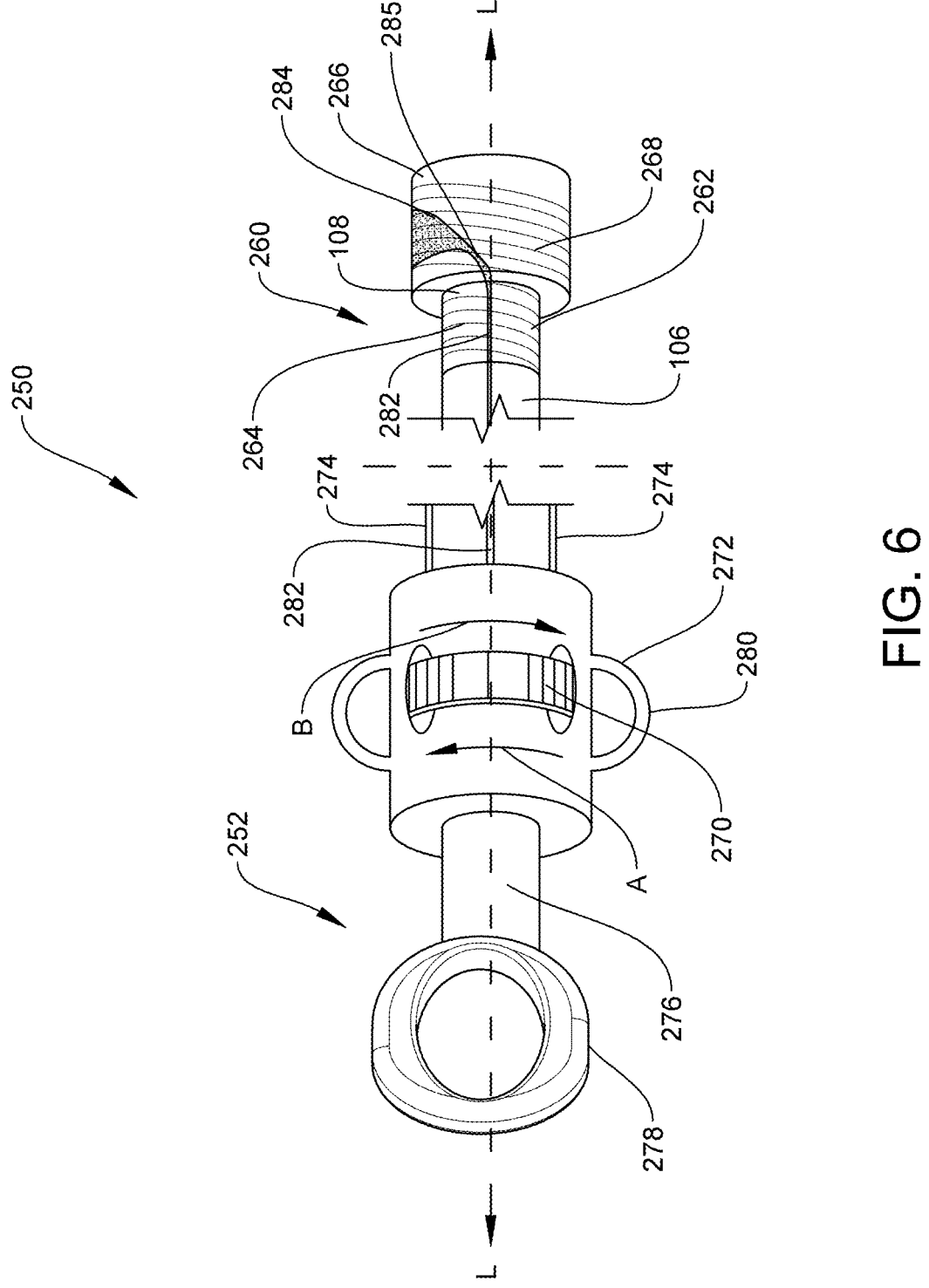
FIG. 6 shows a perspective view of a system according to a still further embodiment.

As shown in FIG. 6, a system 250 includes a handle 252 and an adapter 260 similar to the adapter 210 including an inner member 262 with a helical ridge 264 protruding therefrom. An outer cap 266 mounted over the inner member 262 includes a helical groove 268 that slidably receives the ridge 264 so that the cap 266 may be advanced distally and retracted proximally over the inner member 262 by rotation of the cap 266 over the ridge 264.

Those skilled in the art will understand that this screw mechanism allows a user to achieve any known amount of extension of the cap 266 as the distance the cap is extended distally or retracted proximally per rotation of the cap 266 is known based on the pitch of the ridge 264 and the helical groove 268 in the same manner described above in regard to FIG. 5. The handle 252 of the system 250 includes an actuator 270 that is rotatably mounted on a spool 272 of the handle 252. The proximal ends of extending members 274 are coupled to the spool 272 that is slidably mounted on the body 276 of the handle 252 to operate the extending members 274 in a manner substantially similar to that described in regard to previous embodiments. The handle 252 of this embodiment includes a finger loop 278 while the spool 272 includes a pair of finger loops 280.

However, those skilled in the art will understand that the handle 252 may take any configuration that allows an operator to move the spool 272 relative to the body 276 of the handle 252 as desired to achieve the desired movement of the adapter 260. Those skilled in the art will understand that the spool 272 may also include a locking mechanism so that the position of the spool 272 relative to the body 276 of the handle 252 may be locked which will the lock the position of the adapter 260 relative to the distal end 108 of the endoscope 106. The actuator 270 off this embodiment is rotatably mounted on the spool 272 and is coupled to a rotating wire 282 that extends from a proximal end coupled to the actuator 270 to extend along the endoscope 106 to the adapter 260.

The rotating wire 282 extends into the cap 266 substantially aligned with a longitudinal axis L of the cap 266 and then bends to form a distal portion 285 extend substantially perpendicular to the axis L to a distal end 284 of the rotating wire 282 that is coupled to the cap 266. Thus, when the user wishes to adjust a position of the cap 266 relative to the inner member 262 and the distal end 108 of the endoscope 106, the user rotates the actuator 270 in a first direction A to extend the cap 266 distally relative to the inner member 262 and in a second direction B to retract the cap 266 proximally onto the inner member 262. That is, as the actuator 270 is rotated relative to the spool 272, the rotating wire 282 is rotated around the endoscope 106 and the distal portion 285 of the rotating wire 282 either pushes the cap 266 in the direction A or pulls the cap 266 in the direction B to rotate the cap 266 so that the cap 266 moves over the ridge 264 to advance (distally) or retract the cap 266 (proximally) until the desired position of the cap 266 has been reached.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

8

What is claimed is:

1. A device for treating tissue, comprising:
a handle including a first actuator;
a first control cable extending distally from a proximal end coupled to the first actuator; and
a cap including a mounting structure configured to be removably coupled in an operative configuration on a distal end of an insertion device, the insertion device being configured to be inserted to a target site within a living body,
wherein the cap further includes an extending part movably coupled to the mounting structure for movement between a retracted position in which a distal end of the extending part is received over the distal end of the insertion device and an extended position in which a distal end of the extending part extends distally beyond the distal end of the insertion device, the extending part including a wall defining an internal channel so that, when the extending part is in the extended position, the wall surrounds a space contiguous to the distal end of the insertion device, the extending part being coupled to a distal end of the first control cable so that, actuation of the first actuator moves the extending part between the extended and retracted positions.

2. The device of claim 1, wherein the extending part is slidably received over the mounting structure so that the extending part moves linearly along the mounting structure between the extended and retracted positions.

3. The device of claim 1, wherein the first control cable is configured to be mounted along a length of the insertion device to extend from the cap to the handle and wherein the handle is configured to remain, during use, outside the living body accessible to a user.

4. The device of claim 1, wherein the mounting structure includes a thread and the extending part includes a structure mating with the thread so that rotation of the extending part about the mounting structure in a first direction moves the extending part distally relative to the mounting structure and rotation of the extending part about the mounting structure in a second direction opposite the first direction moves the extending part proximally relative to the mounting structure.

5. The device of claim 4, wherein the first control cable is configured to be inserted through an internal channel of the insertion device to the distal end thereof, the first control cable passing into the extending part via an opening in a radially inner surface of the wall of the extending part and being mounted to the extending part so that, movement of the first actuator moves the first control cable relative to the mounting structure to rotate the extending part about the mounting structure to move the extending part proximally and distally relative to the distal end of the insertion device, the handle being configured to remain, during use, outside the living body accessible to a user.

6. The device of claim 5, wherein the first actuator comprises a wheel coupled to the first control cable and rotatably mounted on the handle so that rotation of the wheel rotates the first control cable.

7. The device of claim 1, wherein the handle further includes at least one feedback structure configured to interact with the first actuator so that a user receives feedback corresponding to actuation of the first actuator corresponding to an amount of movement of the extending part relative to the mounting structure.

8. The device of claim 7, wherein the first actuator is slidably mounted on a body of the handle and the feedback structure includes a series of bumps on the body of the handle which, when contacted by the first actuator, provide tactile or audible feedback to the user.

9. The device of claim 1, further comprising:

a hemostatic clip removably mounted on the extending part and a second control cable extending from the hemostatic clip to a second actuator on the handle so that, when the extending part is moved to the extended position, operating the second actuator moves the second control cable to deploy the hemostatic clip from the extending part to clip any tissue drawn into the channel of the extending part.

10. The device of claim 1, wherein the first control cable includes a longitudinally stiff axially flexible coil.

11. The device of claim 1, wherein the mounting structure includes a first portion having a first outer diameter and a second portion extending distally from the first portion and having a second outer diameter reduced relative to the first outer diameter of the first portion and the extending part having an inner diameter corresponding to the second outer diameter of the second portion and an outer diameter substantially equal to that of the first portion.

12. The device of claim 1, wherein the hemostatic clip includes first and second jaws biased toward a closed configuration and wherein the extending part is sufficiently radially stiff to maintain the hemostatic clip in an open configuration in which the first and second jaws are separated from one another and so that the channel of the extending part remains open to receive tissue to be clipped when in the extended position.

13. A method for treating tissue, comprising:

mounting on a distal end of an endoscope a mounting structure of a cap in a retracted position in which a distal end of the cap is retracted toward the distal end of the endoscope;

advancing the endoscope into a living body to a target site adjacent to tissue to be treated;

operating a first actuator which, during use, remains outside the living body accessible to a user, to extend an extending part of the cap distally relative to the mounting structure so that the extending part projects distally from the distal end of the endoscope with an internal channel of the extending part defining an interior space contiguous with the distal end of the endoscope; and after treating tissue accessed via the internal channel of the extending part, operating the first actuator to retract the extending part to the retracted position.

14. The method of claim 13, wherein operating the first actuator to extend the extending part of the cap distally relative to the mounting structure comprises sliding the first actuator axially relative to a body of a handle on which the first actuator is mounted.

15. The method of claim 13, wherein operating the first actuator to extend the extending part of the cap distally relative to the mounting structure comprises rotating the first actuator about a body of a handle on which the first actuator is mounted.

16. The method of claim 13, wherein the cap includes a hemostatic clip removably received thereon and the method further comprising:

drawing tissue into the internal channel of the extending part; and operating a second actuator that, during use, remains outside the living body accessible to the user, to deploy the hemostatic clip from the extending part to clip the tissue that has been drawn into the internal channel of the extending part.

17. The method of claim 13, wherein actuation of the first actuator moves the extending part linearly over the mounting structure.

18. The method of claim 13, further comprising:

actuating the first actuator in a first direction to rotate the extending part over a threading of the mounting structure to advance the extending part distally relative to the mounting structure; and actuating the first actuator in a second direction opposite the first direction to rotate the extending part linearly over the threading of the mounting structure to retract the extending part proximally relative to the mounting structure.

* * * * *